Figure 1:
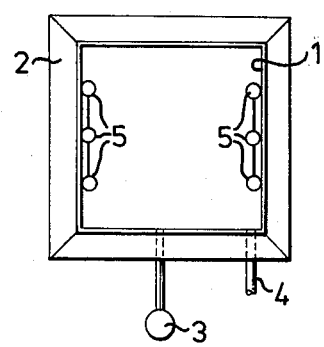

United States Patent [19]

Näsman et al.

[11] 4,296,067
[45] Oct. 20, 1981

[54] METHOD OF STERILIZING MATERIAL, ESPECIALLY BANDAGE AND SURGICAL INSTRUMENTS, IN AN AUTOCLAVE OPERATING WITH VACUUM AND STEAM

[76] Inventors: John O. Näsman, Rapphönsvägen 15,, 122 39 Enskede; Carl-Erik Högfeldt, Tideliusgatan 56, 116 69 Stockholm, both of Sweden

[21] Appl. No.: 116,843

[22] Filed: Jan. 30, 1980

[30] Foreign Application Priority Data

Jan. 30, 1979 [SE] Sweden .............................. 7900813

[51] Int. Cl.³ .............................................. A61L 2/06
[52] U.S. Cl. ....................................... 422/26; 422/299
[58] Field of Search .................... 422/26, 27, 25, 295, 422/297, 298, 299

[56] References Cited

U.S. PATENT DOCUMENTS

1,180,895  4/1916  Way et al. .............................. 422/26
4,164,538  8/1979  Young et al. ........................... 422/26

FOREIGN PATENT DOCUMENTS

2118048  10/1972  Fed. Rep. of Germany ........ 422/26
1086661  10/1967  United Kingdom .................. 422/26

*Primary Examiner*—Barry Richman
*Attorney, Agent, or Firm*—LeBlanc, Nolan, Shur & Nies

[57] ABSTRACT

A method of sterilization of material in an autoclave, at which method pre-vacuum is created during a certain period of time in the autoclave chamber, during the following period of time steam supply and sterilization of the material take place, and during the period of time following thereafter after-vacuum is created. During the entire procedure of said lastmentioned period of time (c) heat is supplied from an extra heat source (5), whereby the temperature at the beginning of the lastmentioned period of time is maintained substantially constant during said entire period (c).

3 Claims, 3 Drawing Figures

METHOD OF STERILIZING MATERIAL, ESPECIALLY BANDAGE AND SURGICAL INSTRUMENTS, IN AN AUTOCLAVE OPERATING WITH VACUUM AND STEAM

This invention relates to a method of sterilizing material, especially bandage and surgical instruments in hospitals, in an autoclave operating with vacuum and steam. It is known that for sterilizing material in an autoclave first the air is sucked off from the material by creating vacuum in the autoclave chamber, whereafter steam is passed into the autoclave chamber for the sterilization, that after a certain time the steam supply is interrupted and again vacuum is created in the autoclave chamber for removing moisture from the material. One disadvantage of this method, however, is that the moisture, which remains during the after-vacuum period after the interruption of the steam supply, is not safely removed so completely from the material that the sterility of the material is reliable. The present invention has the object to establish a method, by which the aforesaid disadvantage is eliminated. This object is achieved in that the method according to the invention is accomplished as follows. It is a method of sterilizing material in an autoclave operating with vacuum and steam and includes the steps in sequence of creating vacuum in the autoclave chamber by connecting a vacuum source to obtain a predetermined pre-vacuum then supplying steam to the autoclave chamber so that the pressure and the temperature rise to the desired values, during the sterilization period, then interrupting the steam supply and creating an after-vacuum in the autoclave chamber for a predetermined period and during substantially the entire after-vacuum period maintaining the temperature, which prevailed in the autoclave during sterilization, substantially constant by supplying heat from a separate heat source, which is preferably electric elements (5), and at the end of the after vacuum period lowering the temperature slightly, for example 20°.

Figure 2:
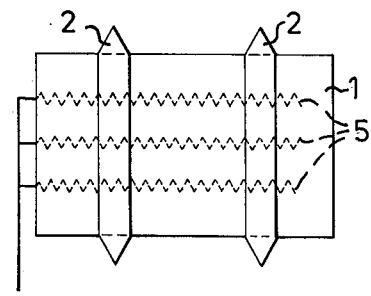
Figure 3:
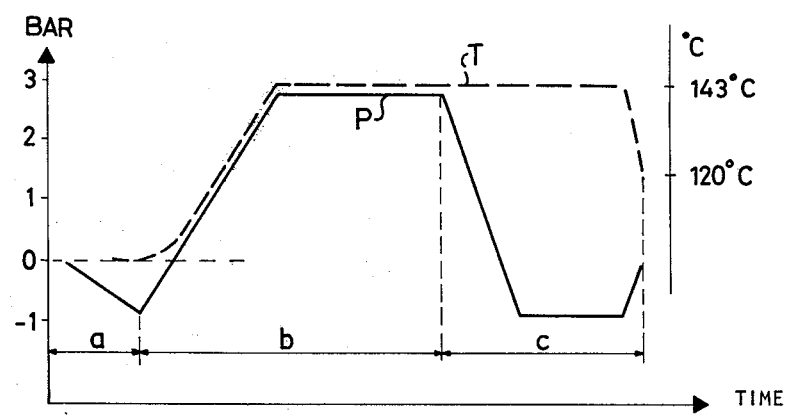

The method according to the invention is explained in the following, with reference to the description of the Figures in the accompanying drawing, of which FIGS. 1 and 2 in a schematical manner show an end view and lateral view, respectively, of an autoclave for carrying out the method according to the invention, FIG. 3 is a diagram with pressure and temperature curves for the autoclave.

The autoclave 1 shown schematically in FIGS. 1 and 2 includes a conventional autoclave chamber of preferably square or rectangular cross-section and has a door, which sealingly closes said chamber. The door is not shown in the Figures, but is provided in one end wall of the autoclave chamber. About the autoclave chamber 1 two steam shells 2 are attached for controlled steam supply to the autoclave chamber through holes extending into the same. To the autoclave chamber further are connected an adjustable vacuum pump 3 for creating vacuum in the autoclave chamber, and preferably an outlet 4 and possibly a conduit (not shown) for the supply of sterile air to the autoclave chamber immediately before the autoclave door is opened for the removal of material placed therein. The autoclave chamber further is provided with electric bar elements 5, which preferably are located along the chamber walls and connected to a current source. The capacity and number of the bar elements are adjusted to the size of the autoclave and to the heat supply required during the intended period of time.

The diagram shown by way of example in FIG. 3 with a pressure curve P and a temperature curve T has a pressure scale at its left-hand and a temperature scale at its right-hand side. The x-axis represents time.

As appears from the pressure curve P in the diagram, first the pressure in the autoclave chamber is reduced as near to vacuum as possible by connecting the vacuum pump 3 for a period of time a, the pre-vacuum period, whereafter the vacuum pump preferably is disconnected. During the period of time b steam is supplied to the autoclave chamber through the steam shells 2, so that the pressure, as shown by the pressure curve P, rises to near to 3 bar at the same time as according to the temperature curve T the temperature increases to preferably 143° C. Thereafter the steam supply is interrupted, and moisture and air are sucked off from the autoclave chamber by the vacuum pump 3 during a period of time c, the after-vacuum period, as appears from the pressure curve P. By connecting the electric elements 5 at the beginning of the period c (or shortly before), the heating to 143° C. is maintained, as the temperature curve shows, during the after-vacuum period and first at the end thereof drops to 120° C. The method described renders it possible to obtain the essential advantage, that by maintaining the heat on said level during the after-vaccum period it is reliably ensured that all moisture of the material in the autoclave is completely removed, contrary to what is the case at known methods where a small amount of moisture can remain at the material after its treatment during the after-vacuum period. The diagram in FIG. 3 is intended to illustrate only an example. The pressures and temperatures indicated may have somewhat different values, and also the periods of time shown may have a different relation to each other. The pre-vaccum period as known may have varying vaccum percentage until the desired vacuum is achieved. The steam may be replaced by or mixed with one or more other media. The electric elements may be replaced by some other heat emitter.

What is claimed is:

1. A method of sterilizing material in an autoclave operating with vacuum and steam, consisting of the steps in sequence of creating vacuum in the autoclave chamber by connecting a vacuum source thereto until a predetermined pre-vacuum has been obtained, supplying steam to the autoclave chamber so that the pressure and the temperature rise to desired values during the sterilization period, interrupting the steam supply and creating an after-vacuum in the autoclave chamber, characterized in that during substantially the entire after-vacuum period the sterilization temperature prevailing in the autoclave chamber at the beginning of the after-vacuum period is maintained substantially constant by supplying dry heat in the chamber from a separate dry heat source and at the termination of the after-vacuum period, and as the vacuum is permitted to terminate, lowering the temperature slightly.

2. A method of sterilizing material as defined in claim 1, wherein the separate dry heat source is supplied by electric elements within the chamber.

3. A method as defined in any of claims 1 or 2, wherein the slight lowering of temperature at termination of the after-vacuum period is in the order of 20° C.

* * * * *